(12) United States Patent
Lemer (10) Patent No.: US 6,358,270 B1
(45) Date of Patent: Mar. 19, 2002

(54) STERNUM CLOSURE DEVICE (75) Inventor: Joseph Lemer, Haifa (IL)

(73) Assignee: Haifa Surgical Instruments Ltd., Haifa (IL)

( * ) Notice: Subject to any disclaimer, the term of this patent is extended or adjusted under 35 U.S.C. 154(b) by 4 days.

(21) Appl. No.: 09/626,802

(22) Filed: Jul. 27, 2000

(51) Int. Cl.[7] ............................................. A61B 17/04
(52) U.S. Cl. ....................... 606/216; 227/19; 227/175.1
(58) Field of Search ................................ 606/216, 219, 606/221; 227/19, 175.1

(56) References Cited

U.S. PATENT DOCUMENTS

| 4,122,989 A | 10/1978 | Kapitanov | 227/108 |
| 4,481,960 A | 11/1984 | Brooks | 131/336 |
| 4,512,346 A | 4/1985 | Lemole | 128/335 |
| 4,585,341 A | 4/1986 | Woodfield | 356/28.5 |
| 5,163,598 A | * 11/1992 | Peters et al. | 227/176 |
| 5,342,396 A | 8/1994 | Cook | 606/219 |
| 5,356,417 A | 10/1994 | Golds | 606/151 |
| 5,462,542 A | 10/1995 | Alesi | 606/151 |
| 5,667,527 A | 9/1997 | Cook | 606/220 |
| 5,849,012 A | 12/1998 | Abboudi | 606/57 |
| 6,007,538 A | 12/1999 | Levin | 606/69 |
| 6,030,410 A | 2/2000 | Zurbrugg | 606/219 |

* cited by examiner

*Primary Examiner*—Gary Jackson
(74) *Attorney, Agent, or Firm*—Rashida A. Karmali (57) ABSTRACT

A sternum closure device for securing parts of severed sternum, such as a human sternum following surgery. The device includes an anvil, capable of forming staples, a bracket positioned opposite the anvil, an instrument for creating openings in the sternum and a mechanism for feeding, mounting and applying the staples. The bracket is joined with the anvil through a displacement mechanism. The instrument for forming opening is designed as a bit brace having a reducing gear and two chucks, to enable concurrent drilling of openings in both severed parts of the severed sternum. The mechanism for feeding and mounting the staples comprises a ribbed bed, a cartridge containing staples and an instrument for mounting the staples.

34 Claims, 9 Drawing Sheets

FIG. 1

View A

View E

STERNUM CLOSURE DEVICE

FIELD OF THE INVENTION

The present invention relates to medical devices for closure of a severed sternum. In particular, the invention is directed to a sternum closure assemblies and methods for re-approximating split portions of tissue to retain the split portions in adjacent contacting relation to promote healing thereof.

BACKGROUND OF THE INVENTION

During surgery that involves a median sternotomy, for example, open-heart surgery, the sternum is cut longitudinally to allow access to the organs within the thoracic cavity. A partial or median sternotomy is a procedure by which a saw or other comparable cutting instrument is used to make a midline, longitudinal incision along a portion or the entire axial length of the patient's sternum, allowing two opposing sternal valves to be separated laterally. Upon completion of the surgery, the sternum is rejoined and closed securely.

Traditionally, the sternal halves have been closed with stainless steel wires which are wrapped around or through the sternal halves to engage in face-to-face relationship and compressed together while the sternum heals. For example, in one version, a surgical needle with the metal wire is led via both severed parts of a severed sternum and the free metal wire is cut-off. In another version, the wire tips are further led via openings in special staples, to project outside and the tips are twisted together by tightening the suture, U.S. Pat. No. 4,512,346 and U.S. Pat. No. 5,849,012. However, these devices have certain shortcomings, in that they require significant force, are difficult to maneuver and the sharp wire edges sometimes cause injury and eventually, infection to soft tissues.

Other prior art sternum closure assemblies include one or two metal plates, these plates being provided with rows of openings, through which extend the screws, pins, or metal wire, to bring together the severed parts of the sternum. U.S. Pat. No. 4,585,341. These devices have drawbacks in that they are ineffective in fixing the split parts of the severed sternum. Moreover, they are foreign bodies in the thoracic cavity, and they can cause disturbance in blood supply to the osseous tissue, thereby prolonging healing and increasing chances of infection.

The strap assemblies known heretofore incorporate clamps, clasps, bands, strips with or without openings and complex locking mechanisms. U.S. Pat. No. 5,356,417; U.S. Pat. No. 5,462,542; and U.S. Pat. No. 6,007,538. The use of compression prevents problems for blood circulation and soft tissues. Other versions of sternum closure devices use tongs, plugs or guns with anvils, to apply staples through the osseous tissue of the sternum. U.S. Pat. No. 4,122,989; and U.S. Pat. No. 4,481,960. However, these devices suffer from several drawbacks, for example, significant force is required to puncture the osseous tissue and insert a staple. In addition, these prior art devices are imprecise in positioning the staples, and do not permit the anvil to bend the staple through 180° angle. Finally, the devices are cumbersome and cause shaking of the organs in the thoraxic cavity.

A certain amount of emphasis has also been directed towards the use of appropriate staples which minimize healing time, minimize distortion of the material stapled, minimize damage of material stapled, minimize scar tissue formation and achieve uniform compression of stapled material. U.S. Pat. No. 5,342,396 and U.S. Pat. No. 5,667,527. However, these devices suffer from several of the same drawbacks discussed above for earlier models of the sternum closure devices and systems.

It would accordingly be desirable to provide a sternum closure device which is stable in construction and effectively secures the severed parts of sternum or other tissue together, i.e., secures the staples in well defined locations, at a predetermined angle, and at a desirable tension to promote uniform healing of the tissue portions while avoiding complications associated with tissue injury, infection and compression.

SUMMARY OF THE INVENTION

The present invention provides improved devices and methods of joining with staples, the opposite parts of a severed sternum following a median or partial sternotomy that overcomes the above cited problems inherent in previous sternum closure devices. Generally, the present invention is embodied in an anvil for forming the staples, a bracket positioned opposite the anvil, a means for making openings in the tissue, and a mechanisms for feeding and mounting the staples.

According to a first aspect of the invention, a sternum closure device comprises an anvil having an element comprising two slots, said element being used for forming or shaping the staples. A bracket is provided with an additional slot to guide the drilling means and to mount the staples in the sternum. Other improvements to the anvil and bracket include forming elements which facilitate their mounting on the sternum parts. The bracket is provided with a post and a lock, the post having two mutually perpendicular openings and a pin mounted on it, and the lock comprising a housing with a slot, and a spring-actuated locking element with a handle situated in the slot.

According to a second aspect of the invention, the bracket is joined with the anvil through a spring-actuated screw having a handle, said screw being positioned in a threaded opening located in the bracket. Two guides are situated between the anvil and the bracket and parallel to the screw, said guides being installed in the openings of the bracket to facilitate displacement of the bracket with respect to the anvil.

The sternum closure device of the present invention comprises a bit brace with a reducing gear and two chucks having interchangeable drills for simultaneously drilling openings in both parts of a severed sternum. The reducing gear includes a housing, said housing including a basis with a lug, and a cover. The lug is provided with an opening and a slot. A driving gear wheel is installed on a driving shaft, said driving shaft being joined with a pneumatic drive. Two driven gear wheels are in engagement with the drive wheel gear. The driving wheel is fastened on the driving shafts, and chucks with interchangeable drills are installed on these driven shafts.

According to another aspect of the invention, the sternum closure device comprises a mechanism for feeding and mounting the staples, including a carrying element constructed of a bed, said bed having a first and second surface. Two ribs provided with a positive stopper are situated perpendicularly to the bed surface. The bed surface and each rib are provided with slots. The first bed surface is also provided with a lug having a threaded opening and a locking screw. The second and opposite bed surface is designed as a wall having a handle. A sub-assembly used for mounting the staples, is installed on the bed surface, said sub-assembly comprising an L-shaped lever and two spring-actuated posts. Said L-shaped lever has a shaft side and a long side. The two spring-actuated posts are locked on the bed surface and passed through the openings in the shaft side of the L-shape lever. The long side of the L-shaped lever is placed in the slot of the bed surface.

A cartridge is placed between the bed ribs, said ribs having an internal sand an external side. The cartridge comprises slots for the staples and a sprelement situated between the cartridge and the face wall of the bed. The spring-wise element presses the cartridge with staples against a plurality of stoppers installed on the internal side of the bed ribs.

According to a preferred embodiment of the invention, an instrument for drilling openings is installed on the bracket post along with precise and well-controlled mechanism or means for feeding and mounting staples. A compression spring is situated between the instrument for drilling openings and the mechanism or means for feeding and mounting staples. The instrument for drilling opening may be displaced from the bracket post when necessary.

BRIEF DESCRIPTION OF THE DRAWINGS

A more complete understanding of the present invention and the attendant advantages and features thereof will be more readily understood by reference to the following detailed description when considered in conjunction with the accompanying drawings wherein.

DETAILED DESCRIPTION OF THE PREFERRED EMBODIMENT

Referring to FIGS. 1 to 15, a sternum closure device 1 is shown to provide a system and method for joining two parts 2 and 3, of a severed sternum 4, by means of staples 5, having legs 6 and 7, which are inserted through openings 8 and 9 of the severed sternum 4.

A preferred embodiment of the sternum closure device includes an anvil for forming the staples. This anvil is positioned on the internal side of the severed sternum. A bracket is situated on the outer side of the severed sternum, opposite the anvil. The anvil comprises an element for forming the staples. It is designed to have two slots. In addition, the bracket has a third slot which is intended to guide the drills and for mounting the staples on the sternum. The unique feature about the present invention is that the anvil and the bracket are designed with bends such that these bends facilitate their proper mounting on the sternum.

The bracket is also provided with a rotatable post and a lock. The post is provided with two mutually perpendicular openings and a pin. The lock comprises of a housing with a slot. A spring-actuated locking element having a handle is situated in the slot in the lock housing.

Figure 1:
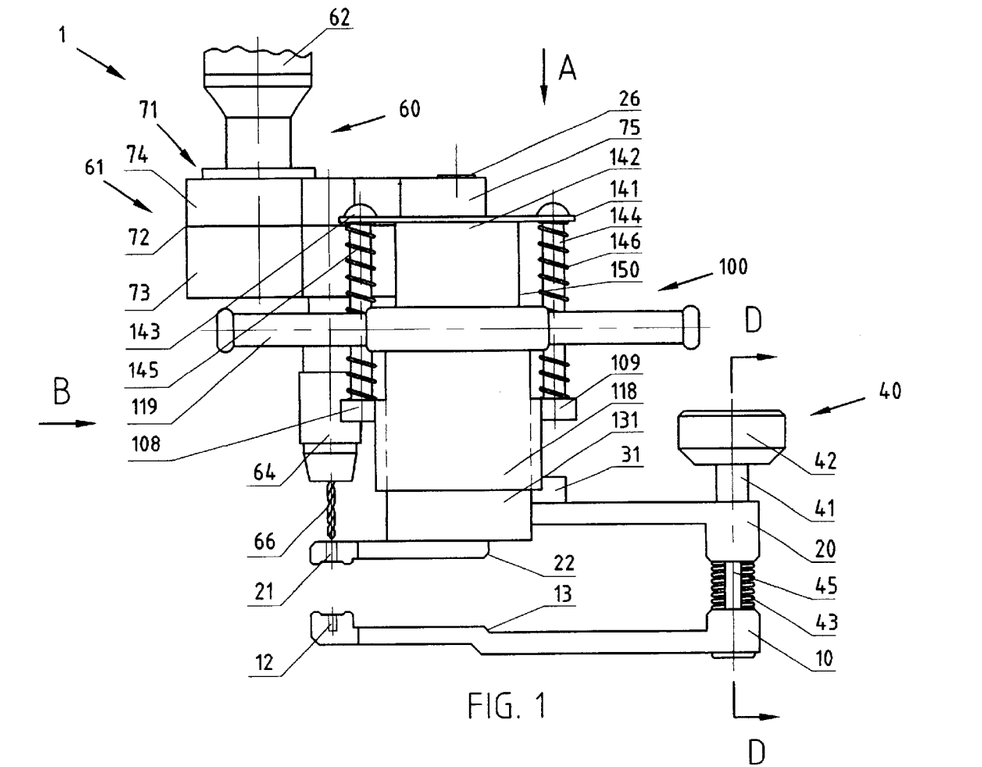
FIG. 1 is a side view of a sternum closure device positioned in the state of drilling openings in the sternum.
Figure 2:
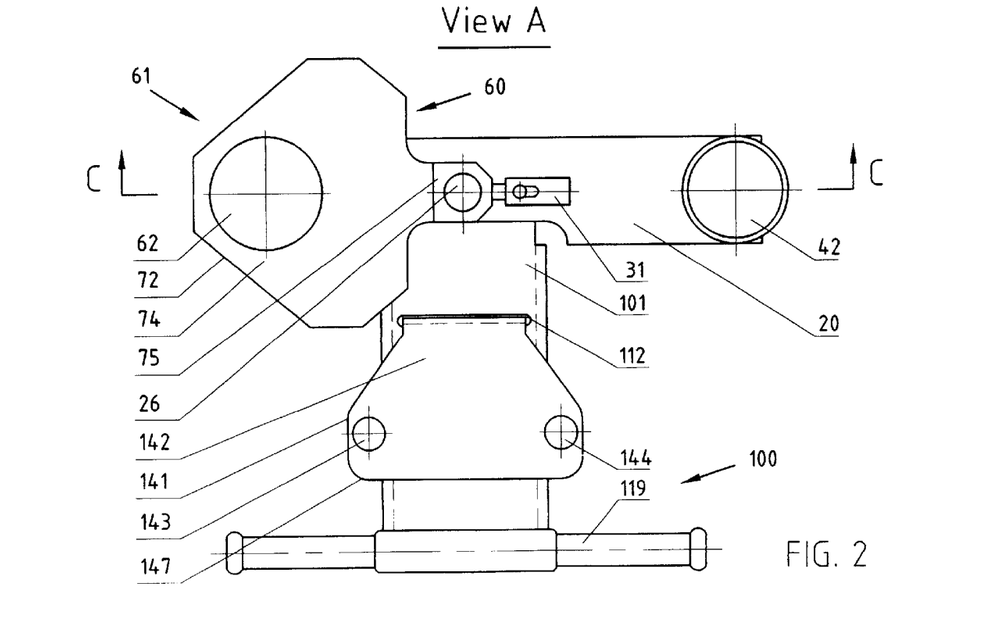
FIG. 2 is a top view of the sternum closure device, taken in the plane of arrow A of FIG. 1.
Figure 3:
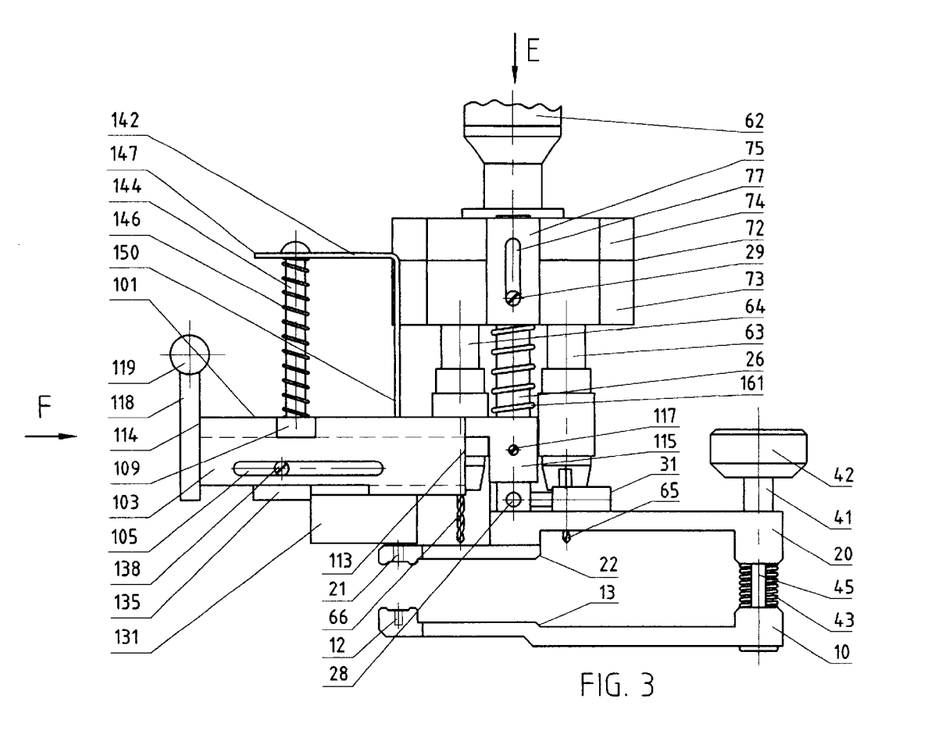
FIG. 3 is a side view of the sternum closure device when it is in the state of mounting staples.
Figure 4:
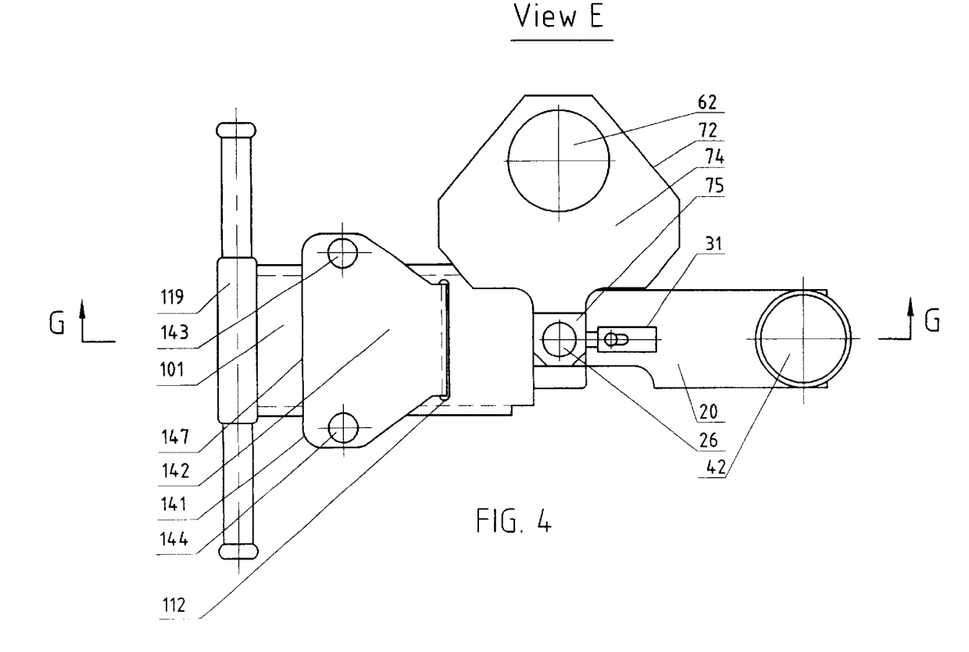
FIG. 4 is a top view of the sternum closure device, taken in the plane of arrow E of FIG. 3
Figure 5:
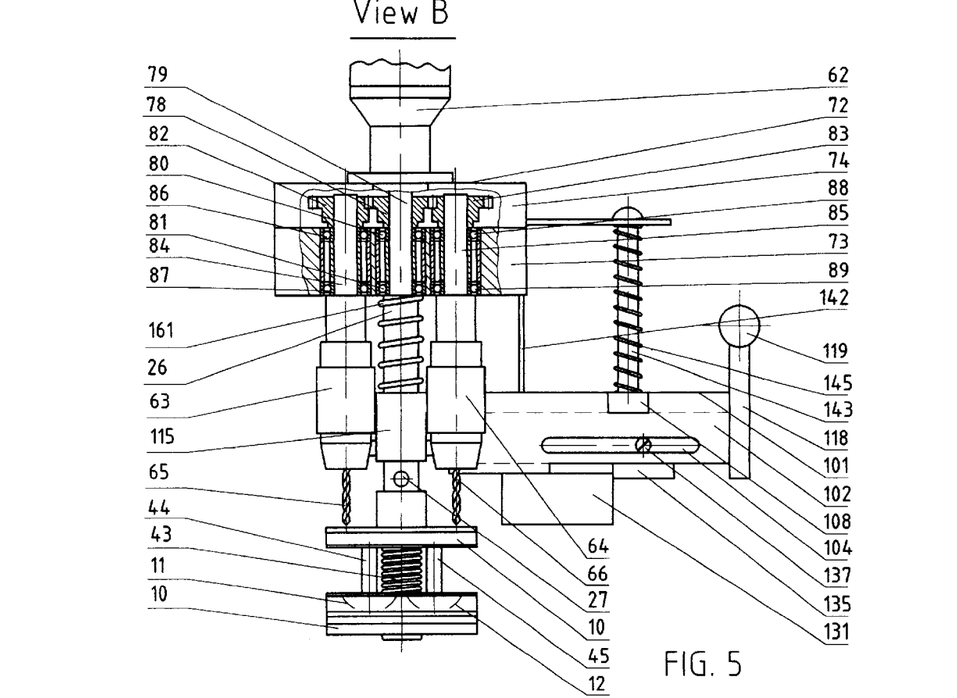
FIG. 5 is a front view of the sternum closure device, taken in the plane of arrow B of FIG. 1.
Figure 6:
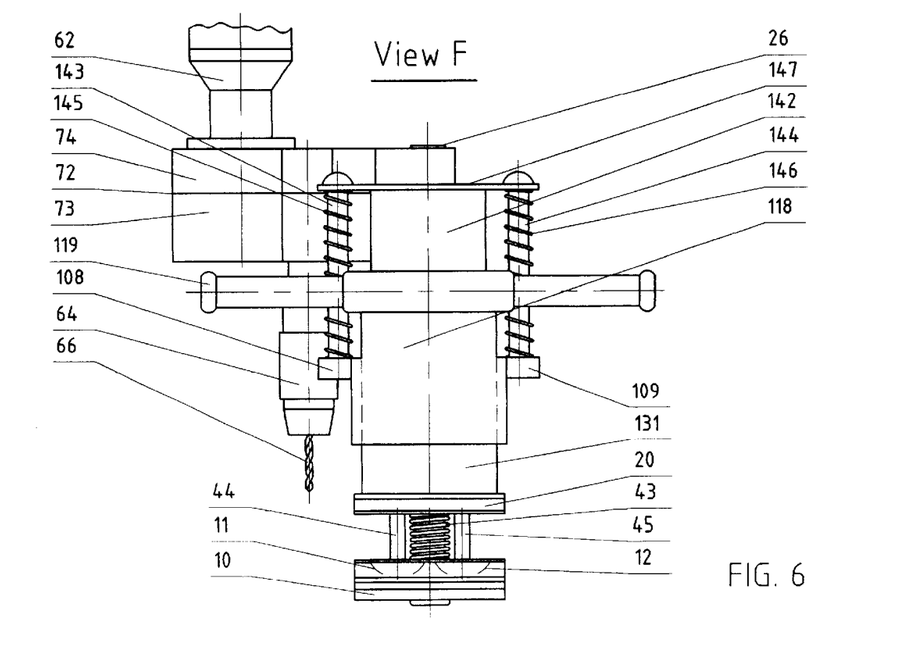
FIG. 6 is a front view of the sternum closure device, taken in the plane of arrow F of FIG. 3.

Referring to FIGS. 1, the sternum closure device 1 comprises of an anvil 10 and a bracket 20, said anvil and said bracket being joined together by a displacement mechanism or means 40. The sternum closure device 1 further comprises of an instrument 60 which is provided to form openings in the sternum 4, and a staple feeding mechanism 100, which is used for feeding and mounting the staples.

Figure 9:
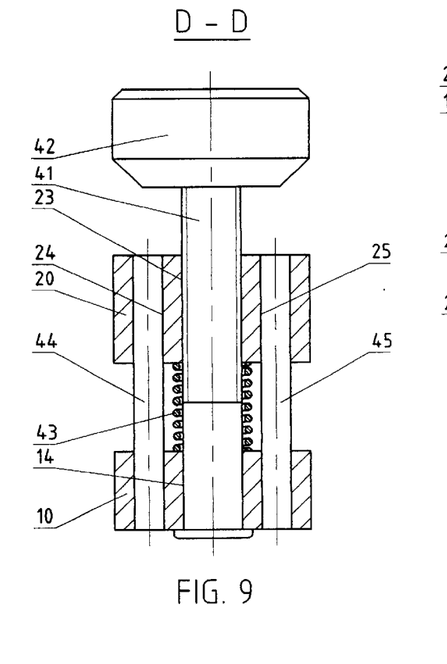
FIG. 9 is a sectional view in the plane of line D—D of a displacement mechanism, which is shown in FIG. 1.

Referring to FIGS. 1 and 9, anvil 10 is provided with two slots 11 and 12 for the purpose of forming staples 5, a bend 13 and a through opening 14 used for joining the displacement mechanism 40. The bracket 20 comprises of a through slot 21, a bend 22 and a threaded opening 23, said opening 23 serving to join the displacement mechanism 40. The bracket 20 further comprises of two through openings 24 and 25, and a cylindrical post 26. The cylindrical post 26 is installed on bracket 20 to provide a turning means, the cylindrical post 26 being further provided with two openings 27 and 28 with mutually perpendicular axes, and a pin 29. A lock 31 is installed traversally to cylindrical post 26 and the lock 31 is fastened on bracket 20.

The bracket is joined to the anvil through a displacement mechanism. This mechanism provides reciprocating displacement of the bracket with respect to the anvil. The displacement mechanism comprises of a spring-actuated screw with a handle. This screw is positioned in the threaded opening in the bracket where it is joined to the anvil. Two guides are situated between the anvil and the bracket. These guides are parallel to the screw and are locked in anvil. The guides are installed in the through openings of the bracket to enable its displacement in the direction of the guides.

Referring to FIGS. 1 and 9, the anvil 10 and bracket 20 are joined via the displacement mechanism 40 to enable reciprocating displacement of bracket 20 to and from the anvil 10. The displacement mechanism 40 comprises of screw 41, said screw 41 extending into a handle 42, a compression spring 43 and two guides 44 and 45. The screw 41 is fastened through a threaded opening 23 in bracket 20, and is locked rotatably in the through opening 14 of anvil 10. A spring 43 is installed between the anvil 10 and the bracket 20, coaxially to the screw 41. Guides 44 and 45 are locked onto the anvil 10 and are in a parallel position to screw 41. Guides 44 and 45 are installed in such a way through openings 24 and 25 of bracket 20 to enable displacement of bracket 20 along guides 44 and 45.

Figure 10:
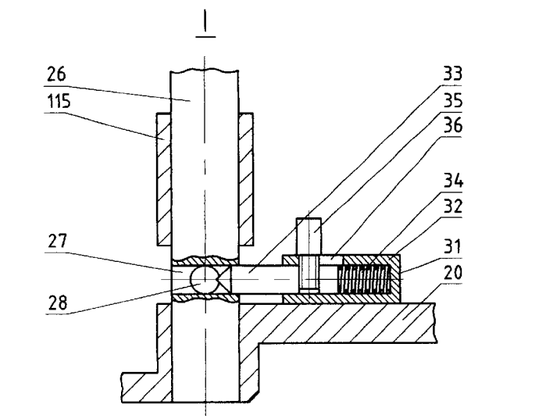
FIG. 10 is a view following detail 1, which is shown in FIG. 7.

Referring to FIG. 10, lock 31 comprises of housing 32, a locking element 33, a spring 34 and a handle 35. The locking element 33 and the spring 34 are introduced partially into housing 32, and the locking element 33 is prevented from dropping out by the handle 35, said handle 35 being installed in a slot 36 located in the housing 32.

In a preferred embodiment of the sternum closure device, the instrument for formation of openings in the sternum comprises one of following mechanisms of the group: a menual bit brace, a pneumatic bit brace, a laser perforator or an ultrasound perforator. The bit brace comprises of a reducing gear and two chucks. These chucks have interchangeable drills for simultaneously drilling openings in both parts of the severed sternum, which are to be joined.

The reducing gear consists of a housing. The housing includes a basis with a lug and a cover. The lug is provided with a through opening and a slot. A driving gear wheel installed on a driving shaft. A driven gear wheels installed on a driven shafts. The driving shaft is then joined to a pneumatic drive. Chucks with interchangeable drills are nstalled on the driven shafts.

Referring to FIGS. 1, 2, 5, 7 and 7a, an instrument 60 is provided for formation of openings. The instrument 60 is constructed as a bit brace 61 with a pneumatic drive 62 and two chucks 63 and 64. The two chucks are provided for mounting interchangeable drills 65 and 66. The instrument 60 further comprises a reducing gear 71. Reducing gear 71 is installed over housing 72, said housing 72 comprising of a basis 73 and a cover 74. Basis 73 is provided with lug 75, said lug 75 having an openi76 and a slot 77. A driving gear wheel 78 is arranged the space of housing 72, and installed on a driving shaft 79. The driving shaft 79 is mounted on basis 73 of housing 72 by means of bearings 80 and 81. Two driven gear wheels 82 and 83, engaged with the driving gear wheel 78, are installed on a driven shafts 84 and 85. The driven shafts 84 and 85 are mounted on basis 73 of housing 72 by means of bearings 86, 87, 88 and 89. The driving shaft 79 is further joined with the pneumatic drive 62, said drive 62 being designed as a pneumatic motor. Chucks 63 and 64 are installed on driven shafts 84 and 85 and these chucks are used for mounting the interchangeable drills 65 and 66.

Instrument 60 and pin 29 are installed on cylindrical post 26 to enable displacement along the cylindrical post 26. The pin 29 is locked on cylindrical post 26 via slot 77 of lug 75 of reducing gear 71. Thus, pin 29 limits the magnitude of displacement of instrument 60 and prevents its turning around post 26.

A mechanism of feeding and mounting the staples is constructed as a bed with two ribs situated perpendicularly to the bed surface. The ribs are provided with a positive stopper. The bed surface and each rib are provided with through slots. One bed surface is provided with a lug, the lug having a threaded through opening and a locking screw in it. The other bed surface is designed as a wall with a handle.

Referring to FIGS. 3, 4, 6, 8, 8a and 12, a feeding and staple mounting mechanism 100 comprises of a carrying element constructed as bed 101 having two ribs 102 and 103. These ribs 102 and 103 are perpendicular to bed 101 and each rib is provided with through longitudinal slots 104 and 105. Stoppers 106 and 107 are installed on the internal side of each rib 102 and 103, respectively. Bed 101 is provided with two lugs 108 and 109, said lugs 108 and 109 in turn are provided with through openings 110 and 111 respectively. Bed 101 is further provided with through slot 112, said slot 112 being placed in parallel to sides 113 and 114 of bed 101. Side 113 is provided with lug 115, which in turn has an opening 116 and a locking screw 117 fastened to the opening 116. Wall 118, having an internal side and an external side, is situated in perpendicular to bed 101 on side 114. Handle 119 is locked to wall 118. A cylindrical support 120 is further installed on the internal side of wall 118.

Mechanism or means 100 further comprises of a cartridge 131 which is positioned between ribs 102 and 103 of bed 101, and a spring 132. Cartridge 131 is designed as a through parallel having slots 133 used for positioning the staples 5. A bracket 135 having an opening 136 is positioned on face side 134 of cartridge 131. Cartridge 131 is installed between ribs 102 and 103 and is held inside the bed 101 by two pins 137 and 138. These two pins 137 and 138 are positioned in slots 104 and 105 of ribs 102 and 103 respectively. Spring 132 is arranged in a cylindrical support 120 of wall 118. It is further inserted partially in opening 136 of bracket 135.

Mechanism or means 100 further comprises subassembly 141, used for mounting the staples. The subassembly 141 comprises a pressure L-shaped lever 142, two posts 143 and 144, and two springs 145 and 146. The L-shaped lever 142 has a short side 147, the short side 147 having two openings 148 and 149. Posts 143 and 144 pass through openings 148 and 149 respectively. Springs 145 and 146 are installed singly on posts 143 and 144 respectively. The subassembly 141 is installed on bed 101. The L-shaped lever 142 has a long side 150, which is introduced in slot 112. Posts 143 and 144 and springs 145 and 146 are locked through openings 110 and 111 of lugs 108 and 109, respectively.

Mechanism or means 100 is mounted on post 26 perpendicularly to instrument 60 and locked in place by a screw 117. In addition, spring 161 is installed on post 26 between mechanism 100 and instrument 60.

Figure 14:
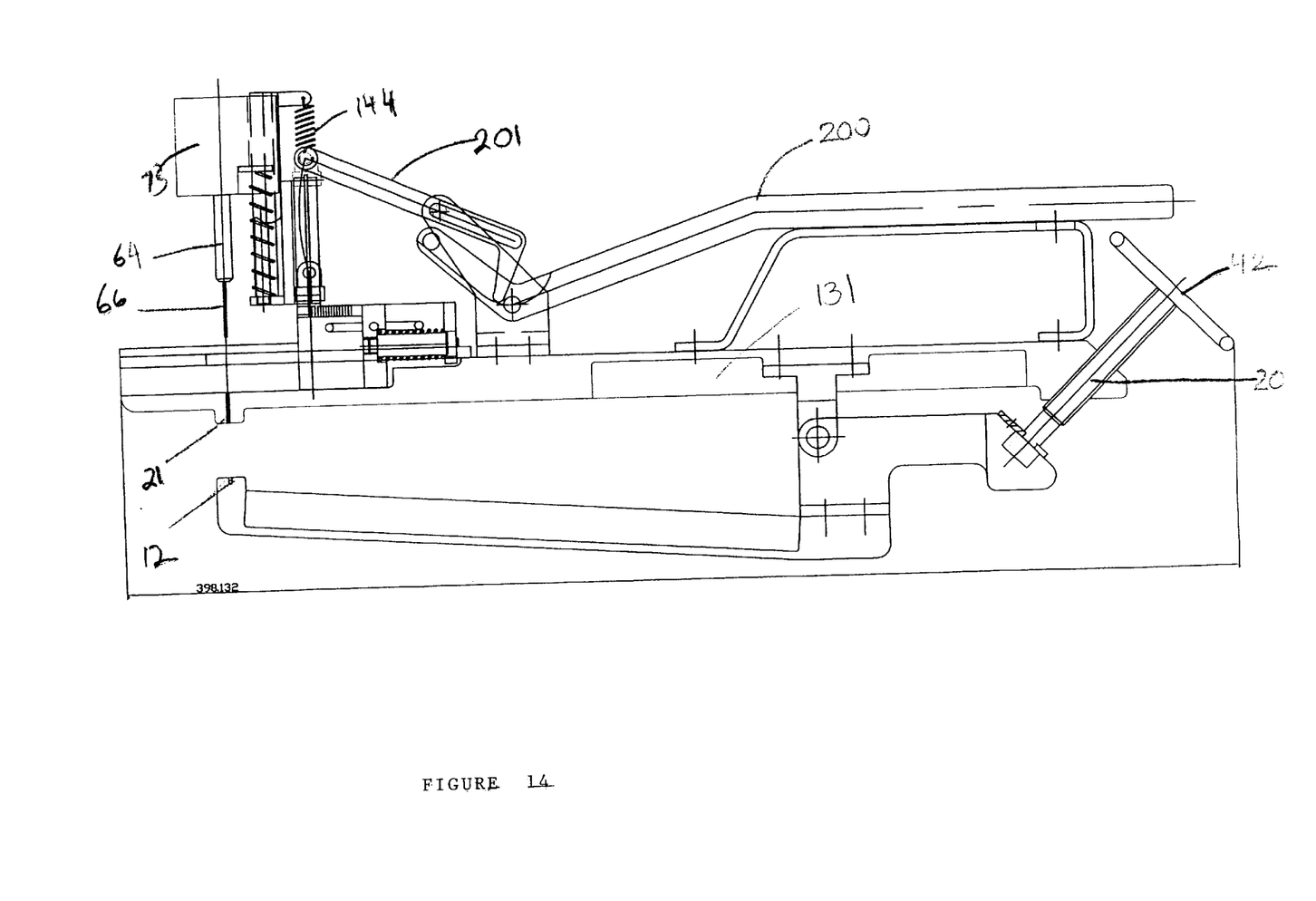
FIG. 14 demonstrates a second embodiment of the invention having a sliding head instead of a rotating head.
Figure 15:
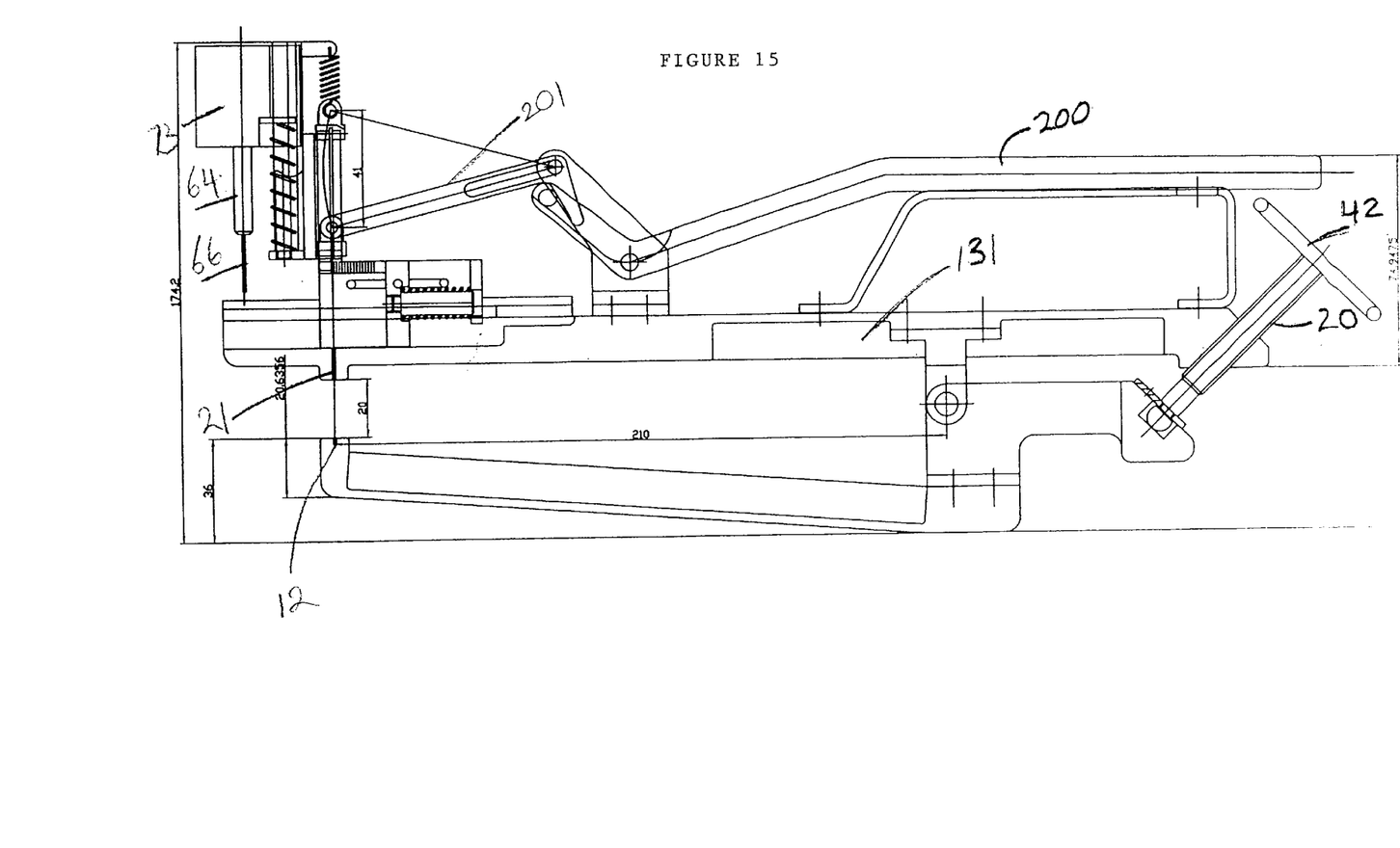
FIG. 15 demonstrates the sliding head of the second embodiment which is used both for drilling and stapling.

FIG. 14 and FIG. 15 represent a second prototype of the invention in which instead of having a rotatable head for alternating the two functions of the device—i.e., drilling and stapling, the two functions are carried out by a sliding head 201 which is located at one end of a stream lined instrument 200. The net effect of this is quicker and simpler alteration of functions and easier handling of the instrument. The cramping of the staples is performed by compressing the ends of the arms of instrument 200 which is easier to do than the rotatable action required in the first embodiment describer earlier.

OPERATION OF THE STERNUM CLOSURE DEVICE

The mode of operation of the sternum closure device is described herein below.

The bracket 20 is moved progressively in direction away from anvil 10 by the displacement mechanism 40 (see FIG. 9). The screw 41 is rotated by handle 42, for example, in an anti-clockwise direction. Bracket 20 moves progressively along guides 44 and 45 in direction away from anvil 10 with releasing spring 43. This results in greater distance between anvil 10 and bracket 20. Anvil 10 and bracket 20 are positioned correspondingly from the internal and external sides of parts 2 and 3 of the severed sternum 4.

Bend 13 of anvil 10 and bend 22 of bracket 20 facilitate mounting anvil 10 and bracket 20 on sternum 4.

With rotation of screw 41 by handle 42 in the opposite direction (in this case—in the clock-wise direction), bracket 20 moves progressively along guides 44 and 45 towards anvil 10. This motion is accompanied with compression of spring 43 and decrease of the distance between anvil 10 and bracket 20 to contact with the internal and external parts 2 and 3 respectively, of the severed sternum 4.

The sternum closure device 1 is arranged in the position of drilling openings in parts 2 and 3 of the severed sternum 4 (FIGS. 1, 2, 5, 7) by lock 31 (FIG. 10).

In the initial state spring 34 of lock 31 is released and the locking element 33 is placed in one of two mutually perpendicular through openings 27 or 28 of post 26 of bracket 20. As displacement handle 35 moves along slot 36, the locking element 33 is removed from the corresponding openings 27 or 28 of post 26 by compression of spring 34. Then post 26 is released from locking and it turns in bracket 20 until the axis of the through opening 27 is aligned with the axis of the locking element 33 of lock 31. While descending handle 35, the compressed spring 34 pushes out the locking element 33 from housing 32. The locking element is introduced in such a way into the through opening 27 of the post 26, that it fixes in a position of the drilling openings.

Figure 7:
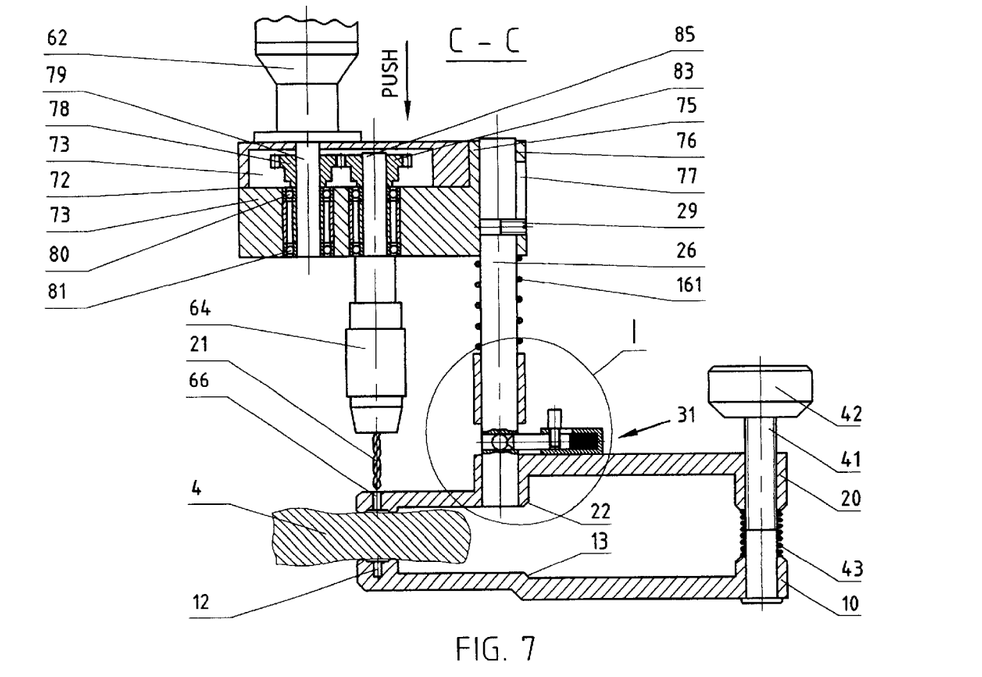
FIG. 7 is a sectional view of the sternum closure device, which is shown in FIG. 2, in the plane of line C—C; this device is in the state preceding drilling the openings in the sternum.
Figure 7A:
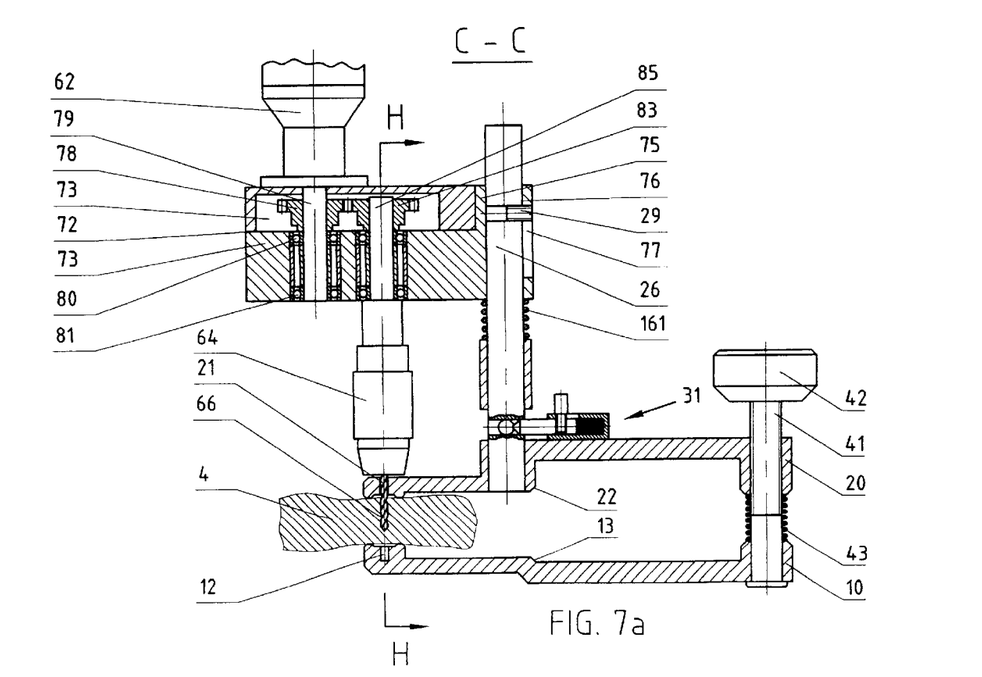
FIG. 7a is a sectional view of the sternum closure device, which is shown in FIG. 2, in the plane of line C—C; this device is in the process of drilling the openings in the sternum.
Figure 11:
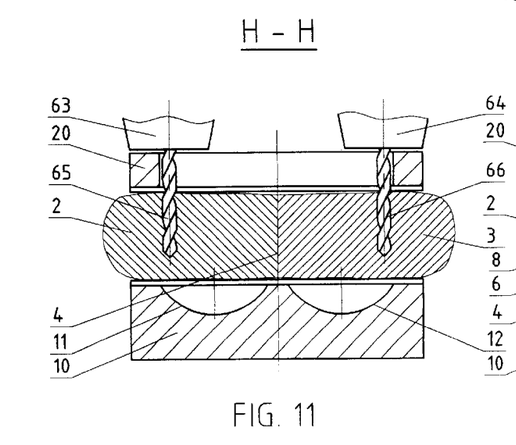
FIG. 11 is a sectional view of the sternum closure device, which is shown in FIG. 7a, in the plane of line H—H.

Drilling openings 8 and 9 are performed in parts 2 and 3 of the severed sternum 4 (FIGS. 7, 7a) by instrument 60 intended for drilling openings. This instrument is installed on post 26 of bracket 20 to allow its reciprocating motion along post 26. Then the pneumatic motor 62 is switched on. The motor via the driving gear wheel 78 and two driven gear wheels 82 and 83 of reducing gear 71 causes two chucks 63 and 64 to rotate with drills 65 and 66 respectively (FIG. 7). By pushing in direction of arrow PUSH onto cover 74 of reducing gear 71 of instrument 60, the bit brace 61 is displaced along post 26 of bracket 20 toward anvil 10. This displacement is accompanied by compression of spring 161 and drills 65 and 66, which pass via slot 21 of bracket 20. Openings 8 and 9 are drilled simultaneously correspond to two parts 2 and 3 of the severed sternum 4 (FIGS. 7a, 11). The magnitude of displacement of instrument 60 along post 26 is limited by the length of slot 77 and the limiting pin 29 (FIGS. 7, 7a). With completion of drilling opening 8 and 9 (FIG. 11), compression on instrument 60 is stopped. It returns to its initial position by release of spring 161 (FIG. 7).

Then the sternum closure device 1 is transferred in the state of mounting staples 5 in sternum 4 (FIGS. 3, 4, 6, 8) by lock 31 (FIG. 10). With displacement of handle 35 of lock 31 along slot 36, the locking element 36 is removed from the through opening 27 of post 26, and compresses spring 34. Then post 26 is released and it is turned in bracket 20 until the axis of the through opening 28 is aligned with the axis of the locking element 33 of lock 31. With descending handle 35 the compressed spring 34 pushes out the locking element 33 from housing 32. Then this locking element is introduced into the through opening 28 of post 36 fixings in such a way that it facilitates mounting of the staples.

Figure 8:
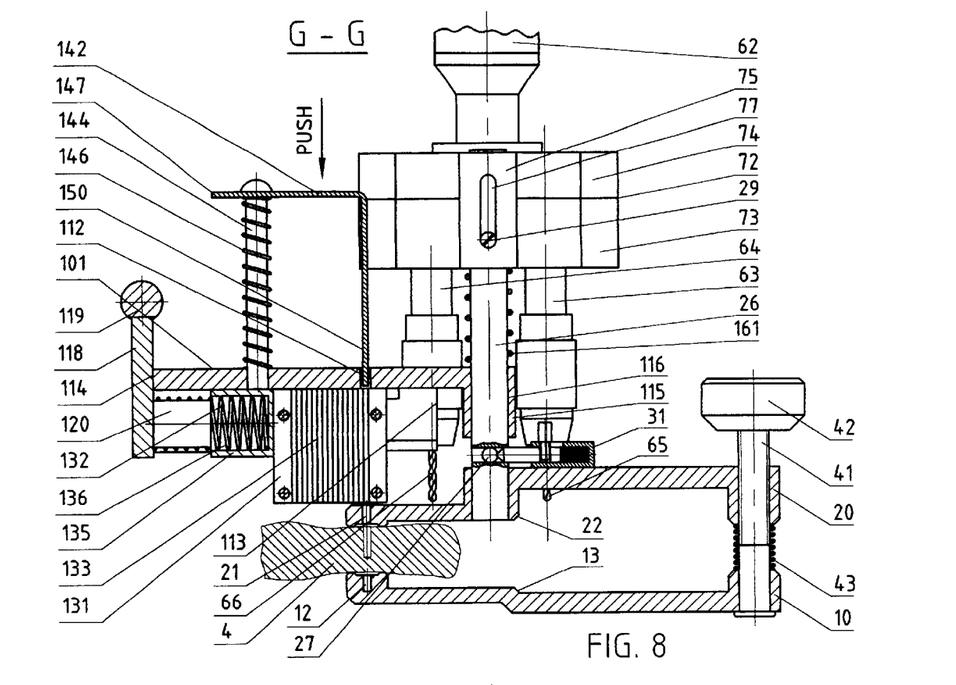
FIG. 8 is a sectional view of the sternum closure device, which is shown in FIG. 4 in the plane of line G—G; this device is in the state preceding mounting the staples in the sternum.
Figure 8A:
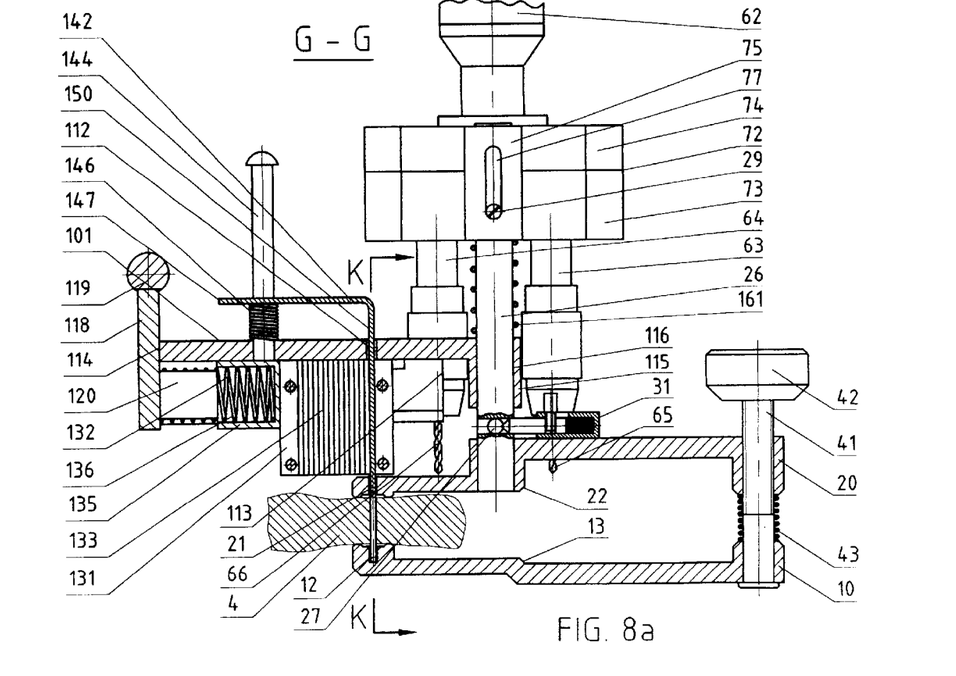
FIG. 8a is a sectional view of the sternum closure device, which is shown in FIG. 4, in the plane of line G—G; this device is in the process of mounting the staples.
Figure 12:
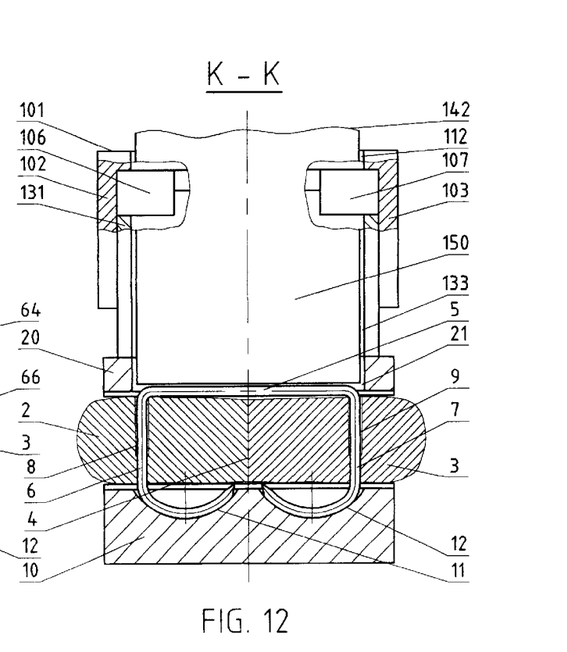
FIG. 12 is a sectional view of the sternum closure device, which is shown in FIG. 8a, in the plane of line K—K.

Mounting staples 5 in the through openings 8 and 9 in respective parts 2 and 3 of the severed sternum 4 (FIGS. 8, 8a) is performed by mechanism 100 of feeding and mounting staples. This is accomplished by locking mechanism 100 on post 26 of bracket 20. Cartridge 131 is filled by staples 5 through slots 133. When mounting the staples 5, the lomechaniis set above the through slot 21 of bracket 20. Staples 5 are forced from cartridge 131 onto stoppers 106 and 107 by spring 132 (FIG. 8). While pushing in direction of arrow PUSH on the short side 147 of the L-shaped lever 142, the lever 142 is displaced along two posts 143 and 144 towards anvil 10. This is accompanied by compression of springs 145 and 146. The long side 150 of the L-shaped lever 142 passes via the through slot 112 and presses out the first staple 5 from the through slot 133 of cartridge 131. This staple is introduced via the through slot 21 of bracket 20 by its two legs 6 and 7 corresponding to openings 8 and 9 in parts 2 and 3 respectively, of the severed sternum 4. With further pushing on the short side 147 of the L-shaped lever 142, legs 6 and 7 of staple 5 pass via openings 8 and 9. The form of legs 6 and 7 is changed with bending owing to slots 11 and 12 of anvil 10, while pulling together parts 2 and 3 of the severed sternum 4 (FIGS. 8a, 12).

The angle in which the two legs of the staple bend is circular and effectively secures the two severed parts of the sternum in a stable grip. The present invention is directed to a sternum closure device which securably retains a plurality of staples around sternum parts to maintain the parts in adjacent engaged relation during healing. The present invention minimizes damage of a tissue stapled and prevents formation of scar tissue.

After mounting of staple 5 is completed (FIG. 5) the compression on lever 142 is terminated. It returns to its initial position owing to release of springs 145 and 146 (FIG. 8). After egress of the long side 150 of L-shaped lever 142 from the through slot 133 of cartridge 131, spring 132 is released. The cartridge 131 is displaced through one further step until the next staple 5 is arranged in through slot 133, with stoppers 106 and 107 (FIGS. 8, 12). In order to mount next staples 5, bracket 20 is displaced progressively away from anvil 10 by the displacement mechanism 40 (FIG. 9). Rotation of screw 41 by handle 42 in an anti-clock wise direction allows displacement of bracket 20 progressively along guides 44 and 45 toward anvil 10. This releases spring 43 and enlarges the distance between anvil 10 and bracket 20.

Then the sternum closure device 1 is made ready for mounting the next staple 5. This process of mounting displacing and compressing staple 5 is repeated as necessary.

Figure 13:
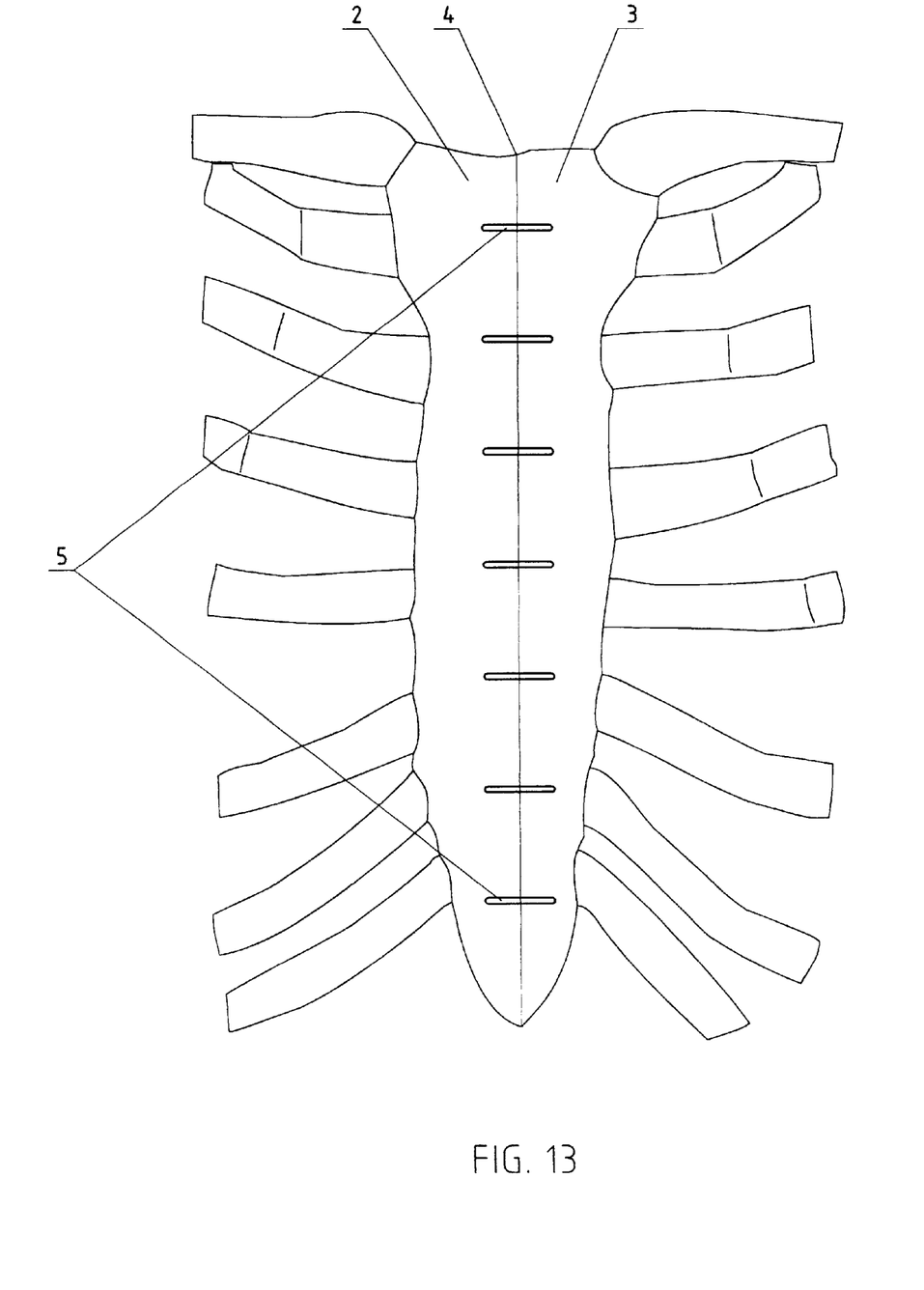
FIG. 13 demonstrates the closed sternum with the set of mounted staples.

When mounting of all required staples 5 is completed (the closed sternum 4 with all mounted staples is shown in FIG. 13), the sternum closure device 1 is removed.

The present invention provides a relatively simple and less traumatic means to effect sternum closure which can be performed rapidly and effectively by the surgeon. While the above description contains many specifics, these specifics should not be construed as limitations on the scope of the invention, but merely as exemplification of preferred embodiments thereof. Those skilled in the art will envision many other possible variations that are within the scope and spirit of the invention as defined by the claims appended hereto.

What is claimed is:

1. A sternum closure device for securing two parts of a severed sternum having an external and internal side, said device comprising:
   a. an anvil to be positioned on said internal side of said severed sternum, said anvil being used for forming the staples,
   b. a bracket to be situated on said external side of said severed sternum,
   c. an instrument for forming openings in said severed sternum, and
   d. a mechanism for feeding and mounting said staples.

2. The sternum closure device as claimed in claim 1, wherein said anvil, which serves for forming the staples, is designed in the form of at least one slot.

3. The sternum closure device as claimed in claim 2, wherein said anvil comprises at least one bend.

4. The sternum closure device as claimed in claim 2, wherein said anvil comprises at least one opening.

5. The sternum closure device as claimed in claim 1, wherein said bracket provides:
   - a post having two openings and a pin mounted on said post, and said post operatively connected to the instrument for forming openings in the severed sternum,
   - a lock comprising of a housing having a slot, a spring actuated locking element having a handle, said handle being situated in the slot.

6. The sternum closure device as claimed in claim 5, wherein said bracket comprises at least one slot.

7. The sternum closure device as claimed in claim 6, wherein said bracket comprises at least one bend.

8. The sternum closure device as claimed in claim 6, wherein said bracket comprises at least one treaded opening and two through openings.

9. The sternum closure device as claimed in claim 5, wherein said post is installed on said bracket with possibility of its turning, said post being provided with two openings with mutually perpendicular axes and with a pin which is fastened on said post.

10. The sternum closure device as claimed in claim 5, wherein said lock is fastened on said bracket and said lock is constructed from a housing and a locking element with handle.

11. The sternum closure device as claimed in claim 10, wherein said housing of said lock comprises as least one slot.

12. The sternum closure device as claimed in claim 11, wherein said locking element with said handle of said lock is provided with a spring-wise element.

13. The sternum closure device as claimed in claim 1, wherein said anvil and said bracket are joined mutually with a displacement mechanism, said displacement mechanism providing reciprocating displacement of said bracket toward said anvil and in back direction.

14. The sternum closure device as claimed in claim 13, wherein said displacement mechanism comprises a screw with a handle, said screw is arranged in said treaded opening of said bracket and is installed on said anvil to enable its rotation.

15. The sternum closure device as claimed in claim 13, wherein said displacement mechanism comprises at least two guides, said guides being arranged between said bracket and said anvil and being fastened on said anvil.

16. The sternum closure device as claimed in claim 15, wherein said guides are installed in said openings of said bracket to allow displacement of said bracket along said guides.

17. The sternum closure device as claimed in claim 13, wherein said displacement mechanism comprises a spring-wise element situated between said anvil and said bracket, with coaxial arrangement of said spring-wise element with respect to said screw.

18. The sternum closure device as claimed in claim 1, wherein said instrument for forming openings in said sternum comprises one of following mechanisms of the group: a manual bit brace, a pneumatic bit brace, a laser perforator, or a ultra-sound perforator.

19. The sternum closure device as claimed in claim 18, wherein said instrument for forming the openings is designed as a bit brace with a reducing gear and is provided with at least two chucks for installation of drills.

20. The sternum closure device as claimed in claim 19, wherein said reducing gear comprises a housing with a lug, and at least three gear wheels are positioned inside said reducing gear.

21. The sternum closure device as claimed in claim 20, wherein said lug of said housing comprises at least one opening.

22. The sternum closure device as claimed in claim 20, wherein one of said gear wheels is in engagement with both others.

23. The sternum closure device as claimed in claim 20, wherein one of said gear wheels is installed on a shaft thereby serving to joining with said drive.

24. The sternum closure device as claimed in claim 1, wherein said mechanism for feeding and mounting said staples comprises a carrying element, an assembly for mounting said staples, a cartridge containing said staples, a plurality of stoppers, and a spring-wise element.

25. The sternum closure device as claimed in claim 24, wherein said carrying element is constructed as a bed with at least two ribs, said ribs being arranged perpendicularly to the surface of said bed and being provided with said limit stoppers.

26. The sternum closure device as claimed in claim 25, wherein each of said ribs is provided with at least one slot.

27. The sternum closure device as claimed in claim 25, wherein said surface of said bed is provided with at least one slot.

28. The sternum closure device as claimed in claim 25, wherein said bed comprises at least one lug which is provided with at least one threaded opening and a locking screw.

29. The sternum closure device as claimed in claim 25, wherein said bed comprises at least one face wall which is provided with a handle.

30. The sternum closure device as claimed in claim 24, wherein said cartridge is provided with slots.

31. The sternum closure device as claimed in claim 30, wherein said cartridge is arranged between said ribs of said bed and said cartridge is provided with two pins which are situated in said slots of said ribs.

32. The sternum closure device as claimed in claim 30, wherein said spring-wise element is arranged between said cartridge and said bed.

33. The sternum closure device as claimed in claim 1, wherein the subassembly for mounting said staples comprises at least one lever and at least two posts which are provided with spring-wise elements.

34. The sternum closure device as claimed in claim 1, wherein the the anvil and the drilling instrument are controlled by a sliding head.

* * * * *